United States Patent [19]
Taylor et al.

[11] Patent Number: 5,866,851
[45] Date of Patent: Feb. 2, 1999

[54] IMPLANTABLE MEDICAL DEVICE WITH MULTI-PIN FEEDTHROUGH

[75] Inventors: William J. Taylor, Anoka; Lynn M. Seifried, Minneapolis; Douglas Weiss, Plymouth; Joseph F. Lessar, Coon Rapids, all of Minn.

[73] Assignee: Medtronic Inc., Minneapolis, Minn.

[21] Appl. No.: 905,788

[22] Filed: Jul. 28, 1997

Related U.S. Application Data

[62] Division of Ser. No. 508,811, Jul. 28, 1995, Pat. No. 5,817,984.

[51] Int. Cl.$^6$ .............................. H01B 17/26; C03C 3/076
[52] U.S. Cl. .................................. 174/152 GM; 65/59.1; 501/55; 501/65; 501/66; 501/67; 501/70; 607/37
[58] Field of Search ..................... 174/152 GM; 65/59.1, 59.34; 501/73, 75, 4, 53, 55, 65, 66, 67, 70; 607/37

[56] References Cited

U.S. PATENT DOCUMENTS

| | | | |
|---|---|---|---|
| Re. 33,170 | 2/1990 | Byers | 607/57 |
| 3,617,316 | 11/1971 | Suzuki | 501/75 X |
| 4,180,700 | 12/1979 | Kraska | 174/152 GM |
| 4,217,137 | 8/1980 | Kraska | 174/152 GM X |
| 4,225,262 | 9/1980 | Koop | 403/272 |
| 4,495,917 | 1/1985 | Byers | 607/57 |
| 4,525,766 | 6/1985 | Peterson | 361/283.1 |
| 4,678,868 | 7/1987 | Kraska | 174/152 GM |
| 4,730,389 | 3/1988 | Baudino et al. | 29/825 |
| 4,816,621 | 3/1989 | Huebner et al. | 174/152 GM |
| 4,874,910 | 10/1989 | McCoy | 174/152 GM |
| 4,940,858 | 7/1990 | Taylor | 174/152 GM |
| 4,951,011 | 8/1990 | Heckaman | 333/33 |
| 4,991,582 | 2/1991 | Byers et al. | 607/2 |
| 5,012,807 | 5/1991 | Stutz | 607/37 |
| 5,076,270 | 12/1991 | Stutz | 607/37 |
| 5,103,818 | 4/1992 | Maston et al. | 607/9 |
| 5,104,755 | 4/1992 | Taylor | 429/181 |
| 5,250,845 | 10/1993 | Runyan | 257/729 |
| 5,294,241 | 3/1994 | Taylor | 65/59.31 |
| 5,306,581 | 4/1994 | Taylor | 429/181 |
| 5,406,444 | 4/1995 | Selfried | 361/302 |
| 5,434,017 | 7/1995 | Berkowitz | 429/94 |

OTHER PUBLICATIONS

"Development of Hermetic Microminiature Connectors", M.K. Neilsen, et al, Journal of Electronic Packaging, Dec. 1991, vol. 113, p. 405.

Primary Examiner—Hyung-Sub Sough
Attorney, Agent, or Firm—Thomas F. Woods; Harold R. Patton

[57] ABSTRACT

A hermetically sealed implantable medical device is provided with a multi-pin arrangement including selected glass to metal or ceramic to metal seals for a feedthrough of the compression seal or matched seal type.

1 Claim, 4 Drawing Sheets

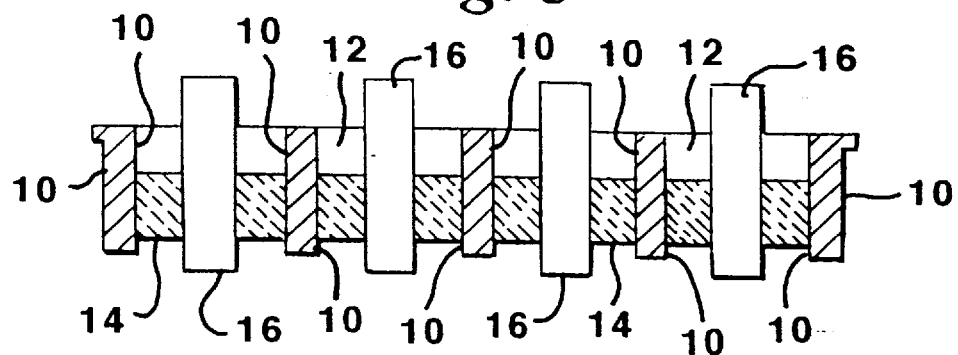
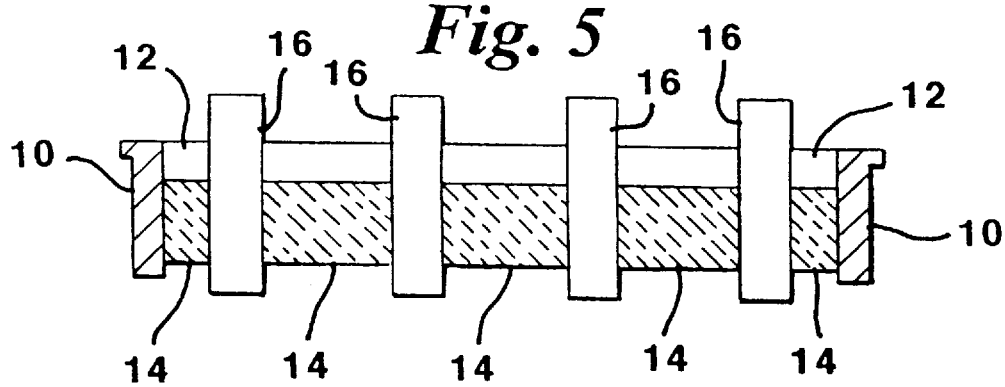
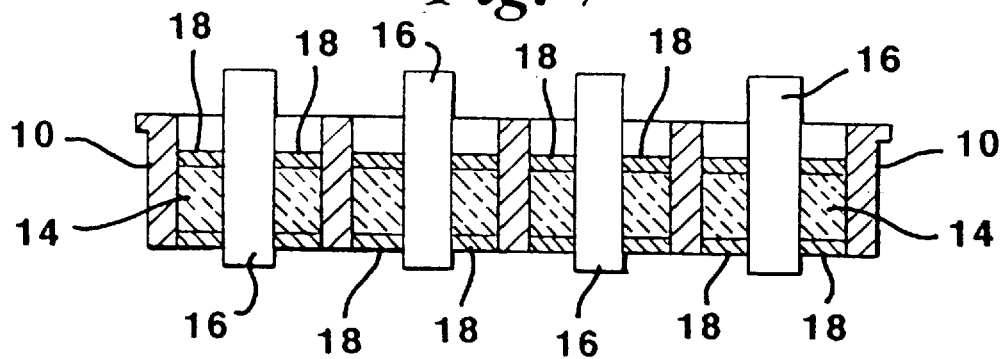

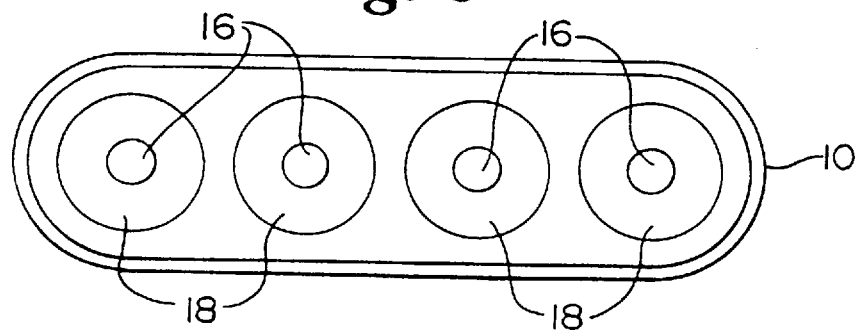
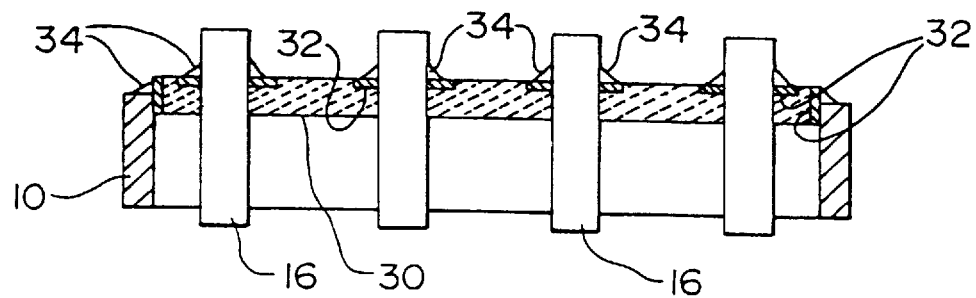

IMPLANTABLE MEDICAL DEVICE WITH MULTI-PIN FEEDTHROUGH

This application is a division of application Ser. No. 08/508,811 filed Jul. 28, 1995 which application is now U.S. Pat. No. 5,817,984

FIELD OF THE INVENTION

This invention relates to electrical feedthrough devices and particularly to multiple lead electrical feedthroughs for providing electrical communication with the interior of a hermetically sealed implantable medical device.

BACKGROUND OF THE INVENTION

There are numerous applications where it is necessary to penetrate a sealed container with a plurality of electrical leads so as to provide electrical access to and from electrical components enclosed within. One such application for which the present invention has particular but not limited utility is in body implantable pulse generators (e.g. for treatment of bradycardia, tachyaiythmia or for muscle or nerve stimulation), referred to generally as implantable pulse generators (IPG's). The heart pacemaker is a well known example of one type of IPG. Typical devices of this type are formed of a metal container housing the electrical and power source components of the IPG with a lid or the like welded to the container to close the device and provide it with a hermetic seal. An electrical lead is electrically connected to the IPG by means of attachment to one or more feedthroughs which penetrate the container but maintain the hermetically sealed environment thereof. A typical feedthrough consists of an external metal part (a frame or ferrule) into which preformed solid or sintered glass part is sealed. Within the glass part, one or more metal leads (pins) are sealed. Since the reliability of critical implantable medical devices depend on hermetic sealing of various components, the integrity of the glass to metal seals used in battery components and the seal between the internal electrical components and the human body is of paramount importance.

In many implantable medical devices, metals which have long term corrosion resistance and biocompatibility are needed to provide years of reliable service since maintenance or repair possibilities for the devices are extremely limited. Moreover, since such devices are sometimes life-saving for the patient, failures of the feedthrough materials can have catastrophic consequences. Therefore, metals like titanium, niobium, tantalum, platinum and the like are used due to their well known superior corrosion resistance and biocompatability.

As such devices have undergone development, they have become smaller yet more electronically sophisticated, making it necessary to include more and more functions into smaller and smaller containers. This translates into a need for multi-pin feedthroughs carried by small, usually slim, containers. Multi-pin arrangements of feedthrough pins have generally been suggested before. For example, in U.S. Pat. No. 4,874,910 issued to McCoy, a number of flat pins are shown traversing a hermetic glass seal in a linear array. Or, in Neilsen et aL "Development of Hermetic Microminiature Connections", *Journal of Elastomeric Packaging,* Dec. 1991, Vol 113/405–409, the stresses on a compression seal for a multi-pin device are modeled. However, the successful combination of materials which include the corrosion resistance and biocompatibility required for an implantable medical device have not been disclosed.

SUMMARY OF THE INVENTION

This invention, by judicious selection and combination of component materials (ferrule, seal insulator and pin) provides for either compression or match seals for electrical feedthroughs, the pins of which are arranged in a multi-pin array together with corrosion resistance and biocompatability needed in an implantable medical device. The resultant feedthrough configuration accommodates at least two arranged pins and may be expanded linearly to any desired number. A linear configuration results in easy identification of the pins and facilitates automated connection therewith and maintains device slimness even when a large number of pins are included in the feedthrough arrangement. The linear arrangement also allows easy access allowing the use of a plug-in electrical connector to facilitate rapid connections to the device components.

BRIEF DESCRIPTION OF THE FIGURES

FIGS. 3 and 4 show a cross-sectional and elevational views respectively of a first configuration according to the invention (separate insulator for each pin).

FIGS. 5 and 6 show a cross-sectional and elevational views respectively of a second configuration according to the invention (common insulator).

FIGS. 7 and 8 show similar views respectively of an optional ceramic disc embodiment.

FIG. 9 is a schematic showing of a metallized ceramic to metal configuration according to the invention

DESCRIPTION OF THE PREFERRED EMBODIMENT

Figure 1:
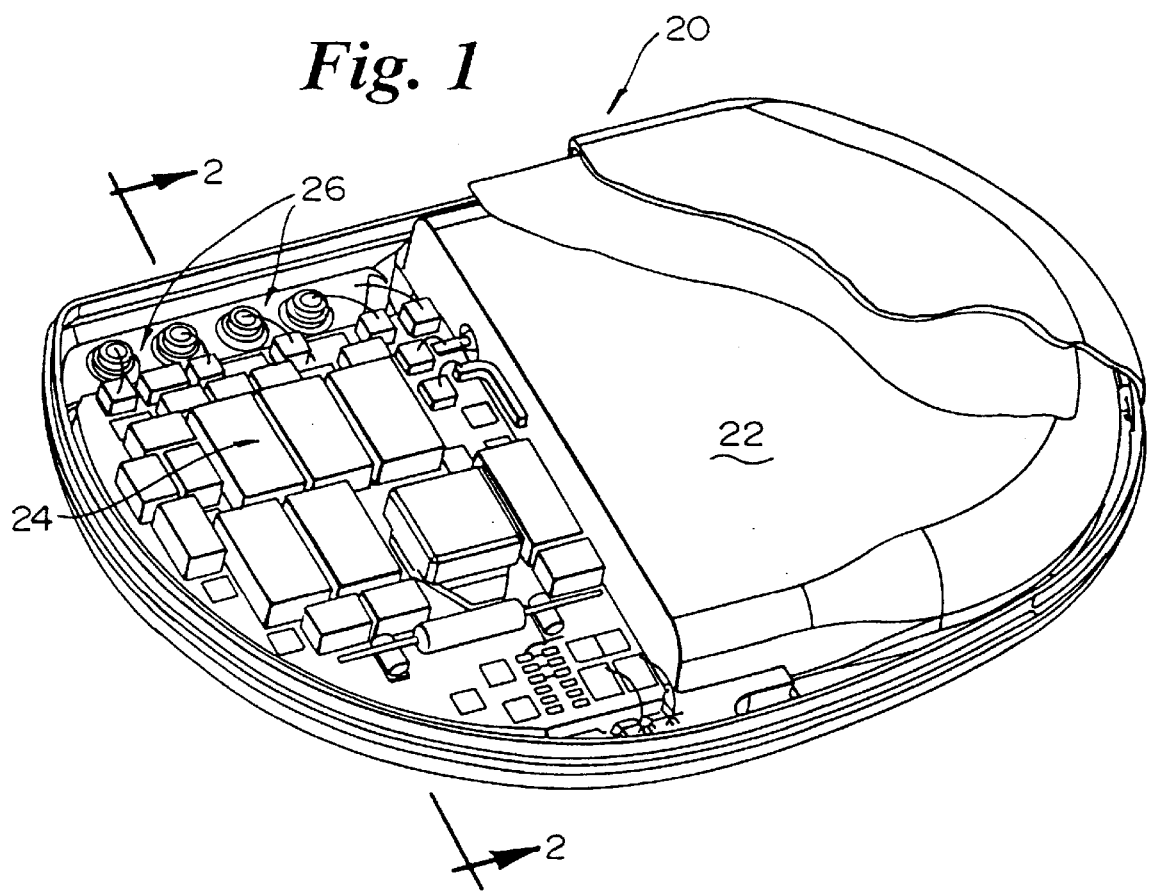
FIG. 1 is a cutaway perspective view of an exemplary IPG.

While this invention may be embodied in many different forms, there are shown in the drawings and described in detail herein specific preferred embodiments as applied to IPG's. The present invention is exemplified as to its principles and is not meant to be limited to the particular embodiments illustrated.

Figure 2:
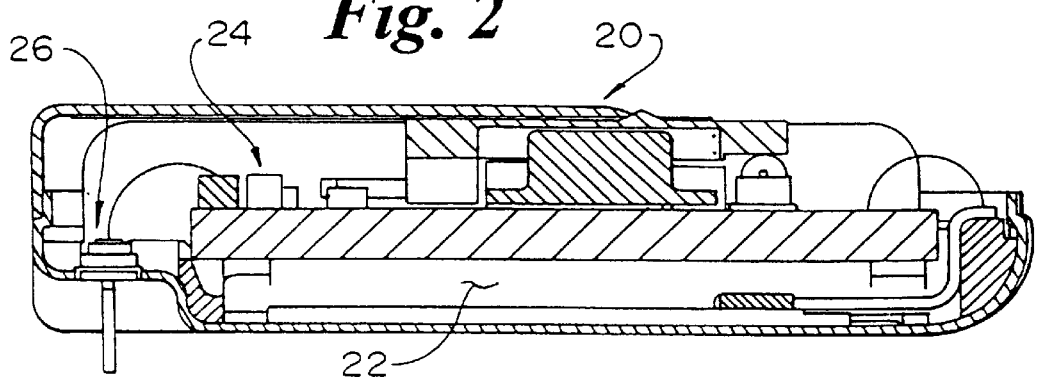
FIG. 2 shows a cross-section taken along line 2—2 in FIG. 1 of the IPG interior and feedthrough.

Referring first to FIGS. 1 and 2, an IPG 20 is shown generically. It includes a battery section 22, a circuit section 24 and a linearly arranged plurality of feedthroughs 26.

Figure 4:
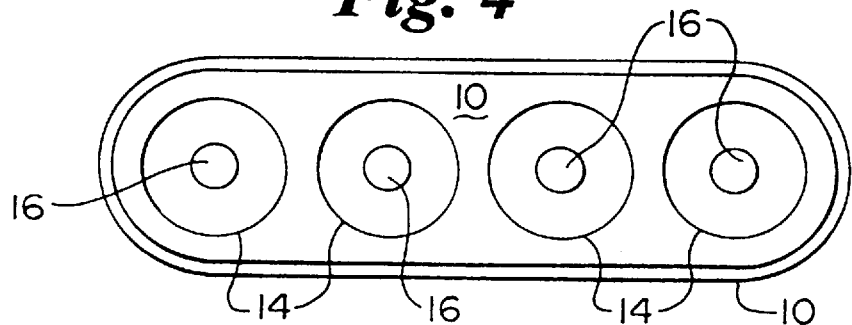

Different feedthrough configurations may be used in the device illustrated in FIGS. 1 and 2 according to this invention and welded into place as a unit in an aperature of the IPG 20. Configurations are shown in FIGS. 3–4 and 5–6. A first linear configuration is shown in FIGS. 3 and 4 having an elongated titanium ferrule 10 having a plurality of openings 12 extending therethrough. The ferrule 10 can be provided by conventional machining, stamping or chemical etching operations, etc. Each of the openings 12 receives a linear array of discrete sealing insulator bodies 14 more specifically described hereinbelow as to choice of materials and which in turn carry a linear array of pins 16 (more specifically disclosed herein below as to choice of materials) which are preferably centered in each of the openings 12.

Figure 6:
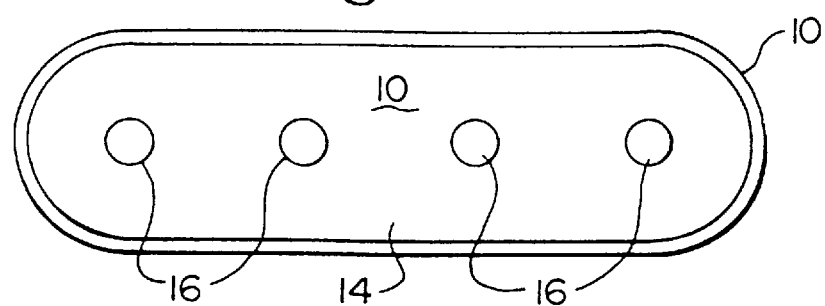

Another linear configuration is shown in FIGS. 5 and 6, also having an elongated titanium ferrule 10 having a single elongated opening 12 therethrough which receives a single elongate sealing body 14 (more specifically described herein below as to materials) and which in turn carries a linear array of pins 16 centered in the opening 12.

Lastly, FIGS. 7 and 8 show an embodiment similar to FIGS. 3 and 4 optionally including an array of discrete upper and/or lower ceramic discs 18 covering the insulators bodies 12 and surrounding pins 16. A similar option (not shown) may be included in the configuration of FIGS. 5 and 6 wherein a simple elongate ceramic disc is included on the upper and/or lower surfaces of the insulator body 14. One purpose of the ceramic body 18 is to provide a platform to control vertical wetting of the glass insulator body in the ferrule (housing), i.e., as the ferrule and glass are heated in a furnace, to keep the glass away from the recessed area which is also the weld zone. This will prevent cracking of the sealing glass during the welding operation later used to install the completed feedthrough in the IPG. Another purpose for the ceramic body is to position the sealing glass, housing and pin when they are heated in the furnace, thereby maintaining the proper location of the elements. Another purpose for the ceramic body is to provide a barrier layer between the sealing glass and the graphite fixturing (not shown) that supports the feedthrough materials during the sealing operation. This keeps the glass from sticking to the fixturing, a problem which may otherwise occur due to deposition of metal vapors onto the fixturing during the glass sealing operation, or the chemical reaction of the molten glass with the fixture material.

Two ceramic bodies similar to the arrangement shown in FIG. 7 may be used to provide electrical insulation with glass in between. Not all glasses deform easily at their sealing temperatures. High viscosity glasses may require mechanical deformation by weights from above. Often this "weight system" requires direct contact with the sealing glass by a non adherent material such as graphite. However, as was stated earlier, with specific glass compositions required when sealing glass to titanium, graphite may not be as non-adherent as desired. Therefore, mechanical deformation of the sealing glass may require providing a "sandwich" with the glass located between the electrically non-conductive material which do not adhere to the graphite but adhere to the glass when sealing occurs.

Choice of Materials

In accordance with this invention the multi-pin arrangement is carried out by the joining methods and material combinations in two particular applications: 1. Glass-to-metal seals; and 2. Ceramic-to-metal seals.

Glass-to-metal seals incorporate an outer ring or ferrule 10 comprised of a weldable grade of titanium or titanium-containing alloy as shown in FIGS. 3–8. The insulator 14 is comprised of a boro-alumino silicate or boro silicate glass with a wide range of thermal expansions to match biostable pin materials such as Tantalum, Niobium, Niobium-Titanium alloy, Platinum, Platinum alloys, Titanium and Titanium alloys. Specific combinations are shown in the Table below.

TABLE

| Glass Type | Weight % Oxide | Glass Thermal Expansion | Equivalent Expansion Pin Material |
| --- | --- | --- | --- |
| Boro-Alumino Silicate (1) | $SiO_2 = 52.0$<br>$Al_2O_3 = 5.0$<br>$B_2O_3 = 26.0$<br>$ZnO = 1.0$<br>$Na_2O = 2.5$<br>$K_2O = 10.0$<br>$TiO_2 = 2.5$ | $6.5 \times 10^{-6}$ in/in/°C. | Tantalum |
| Pemco/Mobay IR63 (2) | $ZrO_2 = 1.0$<br>$SiO_2 = 46.7$<br>$B_2O_3 = 16.6$<br>$Al_2O_3 = 4.4$<br>$ZrO_2 = 9.9$<br>$Na_2O = 7.5$<br>$K_2O = 0.4$<br>$CaO = 14.5$ | $7.8 \times 10^{-6}$ in/in/°C. | Niobium, Niobium/Ti alloy |
| Boro-Alumino Silicate (3) | $SiO_2 = 5{-}10$ (6.7 preferred)<br>$Al_2O_3 = 20{-}30$ (22.8 preferred)<br>$B_2O_3 = 20{-}30$ (23.4 preferred)<br>$CaO = 12{-}17$ (12.5 preferred)<br>$BaO = 0{-}35$ (34.5 preferred)<br>$MgO = 0{-}12$<br>$SrO = 0{-}14$ | $9.0 \times 10^{-6}$ in/in/°C. | Platinum, Titanium (or: Platinum alloys and Titanium alloys) |

Sealing of a ceramic such as $Al_2O_3$ 30 to a linear titanium or niobium/titanium ferrule or housing 10 and niobium or platinum pins 16 is shown in FIG. 9. It is accomplished in a vacuum furnace by first metallizing area 32 on the ceramic 30 and then joining metallized ceramic insulator to pin (16) and ferrule (10) by melting a metal preform such as a gold preform (34) to join the assembly. This process is typically called brazing. The metallizing 32 may be accomplished by sputtering a thin layer of metal such as Niobium (Nb) onto the surface of a ceramic such as alumina ($Al_2O_3$) in appropriate bonding locations as shown. The metallized ceramic $Al_2O_3$ 30 is then brazed to the ferrule 10 and pins 16 using gold as the braze material. It will be appreciated by those skilled in the art that other ceramics and metals can also be used to join the assembly by brazing.

Of the foregoing material combinations in linear array, glass types (1) and (2) and the ceramic type provide reliable compression seals while glass type (3) provides a reliable match seal (relative to the ferrule expansion).

This completes the description of the preferred and alternate embodiments of the invention. Those skilled in the art may recognize other equivalents to the specific embodiments described herein which equivalents are intended to be encompassed by the claims hereto.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An implantable medical device having an hermetically sealed case, comprising:
   a feedthrough hermetically sealed in an aperture of the case, the feedthrough comprising a ferrule of biocompatible, corrosion resistant metal and having an aperture of the ferrule, the insulator bodv comprising a material selected form the group consisting of boro-alumino silicate glass, boro silicate glass, and a ceramic and at least tow pins formed of biocompatible, corrosion resistant metal extending through the aperture of the ferrule in sealing engagement with the insulator body, the insulator body comprising a glass having a nominal composition of about:
$SiO_2$=46.7 wt %
$B_2O_3$=16.6 wt %
$Al_2O_3$=4.4 wt %
$ZrO_2$=9.9 wt %
$Na_2O$=7.5 wt %
$K_2O$=0.4 wt %
$CaO$=14.5 wt % the pins comprising a metal selected from the group consisting of niobium and niobium/titanium alloy.

* * * * *